United States Patent
Weadock

(10) Patent No.: US 11,141,214 B2
(45) Date of Patent: Oct. 12, 2021

(54) THORACOSCOPIC METHODS FOR TREATMENT OF BRONCHIAL DISEASE

(71) Applicant: Ethicon, Inc., Somerville, NJ (US)

(72) Inventor: Kevin Shaun Weadock, Hillsborough, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 16/526,245

(22) Filed: Jul. 30, 2019

(65) Prior Publication Data

US 2020/0000514 A1    Jan. 2, 2020

Related U.S. Application Data

(62) Division of application No. 14/538,930, filed on Nov. 12, 2014, now abandoned.

(Continued)

(51) Int. Cl.
*A61B 18/14*    (2006.01)
*A61B 18/04*    (2006.01)
(Continued)

(52) U.S. Cl.
CPC .......... *A61B 18/1445* (2013.01); *A61B 18/04* (2013.01); *A61B 18/085* (2013.01); *A61B 18/18* (2013.01); *A61N 5/1014* (2013.01); *A61N 7/02* (2013.01); *A61B 18/1815* (2013.01); *A61B 18/20* (2013.01); *A61B 90/361* (2016.02); *A61B 2018/00434* (2013.01); *A61B 2018/00541* (2013.01); *A61B 2018/00613* (2013.01); *A61B 2018/00642* (2013.01);
(Continued)

(58) Field of Classification Search
CPC ... A61B 18/1445; A61B 18/04; A61B 18/085; A61B 18/18; A61B 90/361; A61B 18/1815; A61B 18/20; A61B 2018/00434; A61B 2018/00541; A61B 2018/00613; A61B 2018/00642; A61B 2018/044; A61B 2018/1422; A61B 2018/1435; A61B 2018/144; A61B 2018/1861; A61N 5/1014; A61N 7/02; A61N 2007/003
See application file for complete search history.

(56) References Cited

U.S. PATENT DOCUMENTS

| 5,755,714 A | 5/1998 | Murphy-Chutorian |
| 5,947,984 A | 9/1999 | Whipple |

(Continued)

FOREIGN PATENT DOCUMENTS

| JP | H06-507810 | 9/1994 |
| JP | 2002-541905 | 12/2002 |

(Continued)

OTHER PUBLICATIONS

Lin, J. MD "Bronchial Thermoplasty Devices," (2011). http://emedicine.medscape.com/article/1982296-overview, 3 pgs.

(Continued)

*Primary Examiner* — Bill Thomson
*Assistant Examiner* — Helene Bor
(74) *Attorney, Agent, or Firm* — Frost Brown Todd LLC

(57) ABSTRACT

A method and apparatus for treatment of pulmonary conditions, including a device having an end effector sized and shaped to contact a nerve component on the exterior of a bronchial segment and apply energy to that nerve component.

20 Claims, 10 Drawing Sheets

Related U.S. Application Data

(60) Provisional application No. 61/905,971, filed on Nov. 19, 2013.

(51) Int. Cl.
| | |
|---|---|
| *A61B 18/18* | (2006.01) |
| *A61N 5/10* | (2006.01) |
| *A61B 18/08* | (2006.01) |
| *A61N 7/02* | (2006.01) |
| *A61B 18/20* | (2006.01) |
| *A61N 7/00* | (2006.01) |
| *A61B 18/00* | (2006.01) |
| *A61B 90/00* | (2016.01) |

(52) U.S. Cl.
CPC ... *A61B 2018/044* (2013.01); *A61B 2018/142* (2013.01); *A61B 2018/144* (2013.01); *A61B 2018/1422* (2013.01); *A61B 2018/1435* (2013.01); *A61B 2018/1861* (2013.01); *A61N 2007/003* (2013.01)

(56) References Cited

U.S. PATENT DOCUMENTS

| | | | |
|---|---|---|---|
| 6,692,491 B1* | 2/2004 | Phan | A61B 18/1445 606/41 |
| 7,200,445 B1 | 4/2007 | Dalbec et al. | |
| 7,363,076 B2 | 4/2008 | Yun et al. | |
| 8,483,831 B1 | 7/2013 | Hlavka et al. | |
| 8,529,563 B2 | 9/2013 | Long et al. | |
| 2002/0052602 A1* | 5/2002 | Wang | A61B 18/1445 606/41 |
| 2004/0087940 A1 | 5/2004 | Jahns et al. | |
| 2004/0097792 A1 | 5/2004 | Moll et al. | |
| 2004/0249416 A1 | 12/2004 | Yun et al. | |
| 2006/0036236 A1* | 2/2006 | Rothstein | A61B 18/1442 606/41 |
| 2006/0047278 A1* | 3/2006 | Christian | A61B 18/1492 606/41 |
| 2006/0229594 A1* | 10/2006 | Francischelli | A61B 34/20 606/27 |
| 2008/0039255 A1 | 2/2008 | Jinno et al. | |
| 2008/0183248 A1* | 7/2008 | Rezai | A61N 1/0553 607/62 |
| 2009/0012513 A1* | 1/2009 | Utley | A61B 18/1485 606/21 |
| 2010/0185232 A1* | 7/2010 | Hughett, Sr. | A61B 18/1445 606/207 |
| 2011/0118725 A1 | 5/2011 | Mayse et al. | |
| 2011/0152855 A1 | 6/2011 | Mayse et al. | |
| 2013/0324989 A1 | 12/2013 | Leung et al. | |
| 2014/0018788 A1* | 1/2014 | Engelman | A61B 18/18 606/33 |
| 2014/0277049 A1 | 9/2014 | Rethy et al. | |
| 2015/0141810 A1 | 5/2015 | Weadock | |

FOREIGN PATENT DOCUMENTS

| | | |
|---|---|---|
| JP | 2013-508121 | 3/2013 |
| WO | WO 2011/060200 | 5/2011 |
| WO | WO 2011/127216 | 10/2011 |
| WO | WO 2012/095654 A1 | 7/2012 |
| WO | WO 2013/148217 | 10/2013 |

OTHER PUBLICATIONS

Mahafzah, M. et al. "Bronchial Thermoplasty Periprocedural Care," (2011). http://emedicine.medscape.com/article/2094272-periprocedure, 2 pgs.
Rocha-Singh, Krishna J. "Renal artery denervation: a brave new frontier." *Endovascular Today* 11 (2012): 45-52.
Thoracic Surgery Associates, P.C. (2004). http://chest-surgery.com/disease-info/thoracoscopy.html, 4 pgs.
Australian Office Action dated Aug. 7, 2018 for Application No. AU 2014353275, 4 pgs.
Chinese Office Action, The First Office Action, dated Dec. 25, 2017 for Application No. CN 201480063347.9, 8 pgs.
Chinese Office Action, The Second Office Action, dated Aug. 28, 2018 for Application No. CN 201480063347.9, 9 pgs.
European Examination Report dated Feb. 23, 2018 for Application No. EP 14806507.1, 3 pgs.
International Search Report and Written Opinion dated Feb. 20, 2015 for Application No. PCT/US2014/065138, 13 pgs.
International Preliminary Report on Patentability and Written Opinion dated May 24, 2016 for Application No. PCT/US2014/065138, 8 pgs.
Japanese Office Action, Notification of Reasons for Refusal, and Search Report dated Jul. 31, 2018 for Application No. JP 2016-532099, 19 pgs.
Japanese Office Action, Final Notification of Reason(s) for Refusal, dated Nov. 27, 2018 for Application No. JP 2016-532099, 4 pgs.
Russian Office Action and Search Report dated Jun. 29, 2018 for Application No. RU 2016121165, 8 pgs.
U.S. Appl. No. 61/905,971, filed Nov. 19, 2013.
Australian Office Action dated Jan. 14, 2020 for Application No. 2019213343, 4 pgs.
Chinese Office Action, The Third Office Action, dated Mar. 8, 2019 for Application No. CN 201480063347.9, 9 pgs.
European Summons to Attend Oral Hearing dated Apr. 29, 2019 for Application No. 14806507.1, 5 pgs.
Cuschieri, A. "Variable curvature shape-memory spatula for laparoscopic surgery." *Surgical endoscopy* 5.4 (1991): 179-181.
Canadian Office Action dated Feb. 12, 2021, for Application No. 2,929,660, 4 pages.
Korean Office Action dated Feb. 25, 2021, for Application No. 10-2016-7016297, 7 pages.

\* cited by examiner

THORACOSCOPIC METHODS FOR TREATMENT OF BRONCHIAL DISEASE

This application is a divisional of U.S. patent application Ser. No. 14/538,930, entitled "Thoracoscopic Methods for Treatment of Bronchial Disease," filed Nov. 12, 2014, published as U.S. Pub. No. 2015/0141810 on May 21, 2015, now abandoned, which claims priority to U.S. Provisional Pat. App. No. 61/905,971 filed on Nov. 19, 2013.

FIELD OF THE INVENTION

The present invention relates to methods and devices for treatment of bronchial diseases, including asthma or chronic bronchitis. The invention more directly relates to methods of providing energy to one or more nerves on or near the bronchi and more particularly, application of energy to these nerves through thoracoscopic means.

BACKGROUND

Obstructive pulmonary disease affects millions of individuals in the United States, limiting enjoyment of life and costing billions of dollars to treat. One such disease is asthma, which is a complex inflammatory disorder of the airways characterized by airway hyperresponsiveness and variable airflow obstruction. According to recent estimates, the annual cost of asthma alone is estimated to be nearly $18 billion. Direct costs accounted for nearly $10 billion (hospitalizations being the single largest portion of direct cost) and indirect costs of $8 billion (lost earnings due to illness or death). For adults, asthma is the fourth leading cause of work absenteeism, resulting in nearly 15 million missed workdays each year (this accounts for nearly $3 billion of the "indirect costs" shown above). Among children ages 5 to 17, asthma is the leading cause of school absences from a chronic illness. It accounts for an annual loss of more than 14 million school days per year (approximately 8 days for each student with asthma) and more hospitalizations than any other childhood disease. A person suffering from an asthma "attack" experiences an acute constriction of the smooth muscles lining the bronchi (the passageway for air to get into the lungs), reducing the airway and limiting air flow. Asthma has traditionally been treated through the use of bronchodilation medication, which opens the airway by dilating the bronchi. This, of course, is a short-term solution to a chronic problem. Other pulmonary diseases include, for example, emphysema and chronic bronchitis, which are both considered Chronic Obstructive Pulmonary Diseases (COPD).

Constriction of the bronchial airway is often caused by the firing or activity of nerves, such as in response to an external stimulus or allergen. These nerves are part of the autonomic nervous system, and the nerves to the lungs derive from the vagus nerves near the pulmonary plexuses. The vagus nerves generally run roughly parallel to or lateral to the esophagus and trachea, while the plexuses are in turn further lateral than the vagus nerves. The plexuses lie or near the main bronchi near their bifurcation, and the nerves follow the branching of the bronchial tree within the lung parenchyma.

Medications have been provided to treat bronchial constriction, but unfortunately these medications are only short-term solutions and may be difficult for children and elderly individuals to take. In addition to medication, other therapies have been attempted. One such therapy includes implanting a signal generator to block signals to the bronchus, which inhibits nerve traffic and relieves contraction. This, however, includes the use of an implantable device, which may have complications with implantation and maintenance, among other issues. Bronchial thermoplasty is another therapy that has recently been explored. Bronchial thermoplasty targets the airway smooth muscles or nerves by inserting a bronchoscope into the patient's airway and delivering radiofrequency (RE) energy to the airway wall, thereby reducing the amount of smooth muscle associated with asthmatic constriction. Since it is difficult to control the deposition of energy to a particular layer of the bronchial wall, attempts to deliver RE energy specifically to the smooth muscle cell layer may inadvertently damage the mucosa or nerves on the surface of the bronchi.

Breathing is automatic, and is controlled by the central nervous system. The peripheral nervous system, in contrast, includes both sensory and motor components. The peripheral nervous system conveys and integrates signals from the environment to the central nervous system. The neurons of the peripheral nervous system transmit signals from the periphery to the central nervous system. The lung, for example, is innervated by the peripheral nervous system, which is under central nervous system control. One particular type of stimulation is of the parasympathetic system (constriction). Stimulation of the parasympathetic system leads to airway constriction, blood vessel dilation, and increased glandular secretion. The parasympathetic innervation of the lung originates from the medulla in the brain via the vagus nerve. The vagus nerve descends and forms ganglia at and around the bronchi. Postganglionic fibers from the ganglia then complete the network by innervating smooth muscle cells, blood vessels, and bronchial epithelial cells. Parasympathetic stimulation through the vagus nerve is responsible for the slightly constricted smooth muscle tone in the normal resting lung.

Stimulation of the parasympathetic system causes bronchi or bronchial tubes to constrict, whereas stimulating the sympathetic nervous system produces the opposite reaction (dilation). Disposed around the outer surface of the bronchi are a series of parasympathetic nerves, which gather into a ganglion or plexus. These plexuses lie on or near the main bronchi near their bifurcation, and the nerves follow the branching of the bronchial tree within the lung parenchyma. These bronchial nerves are associated with the vagus nerve, and cause the swelling and inflammation associated with an asthmatic response. Vagal stimulation can also lead to an increase in the activity of the parasympathetic reflex control of the airways, which contributes to greater mucus secretion and bronchial smooth muscle contraction. Thus methods and devices that inhibit or prevent such stimulation may have an additional beneficial effect of reducing symptoms associated with asthma and chronic bronchitis.

It follows that attempts to bronchoscopically apply RF energy to nerves on the external surface of the bronchi may unintentionally damage the mucosa and smooth muscle cells as well. Therefore, even in seemingly successful bronchial thermoplasty treatments, the patient's recovery time is extended due to the damages to the mucosal wall of the bronchi. In fact, patients undergoing this procedure frequently experience several weeks of discomfort before they may experience relief. The present invention seeks to treat pulmonary diseases such as asthma and chronic bronchitis through the use of procedures and devices that apply energy to nerves on the external surface of the bronchi through thoracoscopic methods.

SUMMARY

In one embodiment of the present invention, there is provided an apparatus for treating pulmonary disease including, the apparatus including an extended body having a proximal end and distal end; an end effector at the distal end; and an energy source to provide energy to the end effector; where the end effector is sized and shaped to contact a nerve located on at least a portion of a bronchial segment and to apply energy to a nerve on the exterior surface of the bronchial segment.

In another embodiment of the invention, there is provided a method of treating pulmonary disease including the steps of: thoracoscopically inserting an apparatus into the thoracic cavity of a patient, the apparatus coupled to an energy source and having an end effector secured thereto; aligning the end effector proximal to or in contact with a nerve component present on or near an exterior surface of a bronchial segment; and, applying energy through the end effector to the nerve component.

DETAILED DESCRIPTION

Figure 1:
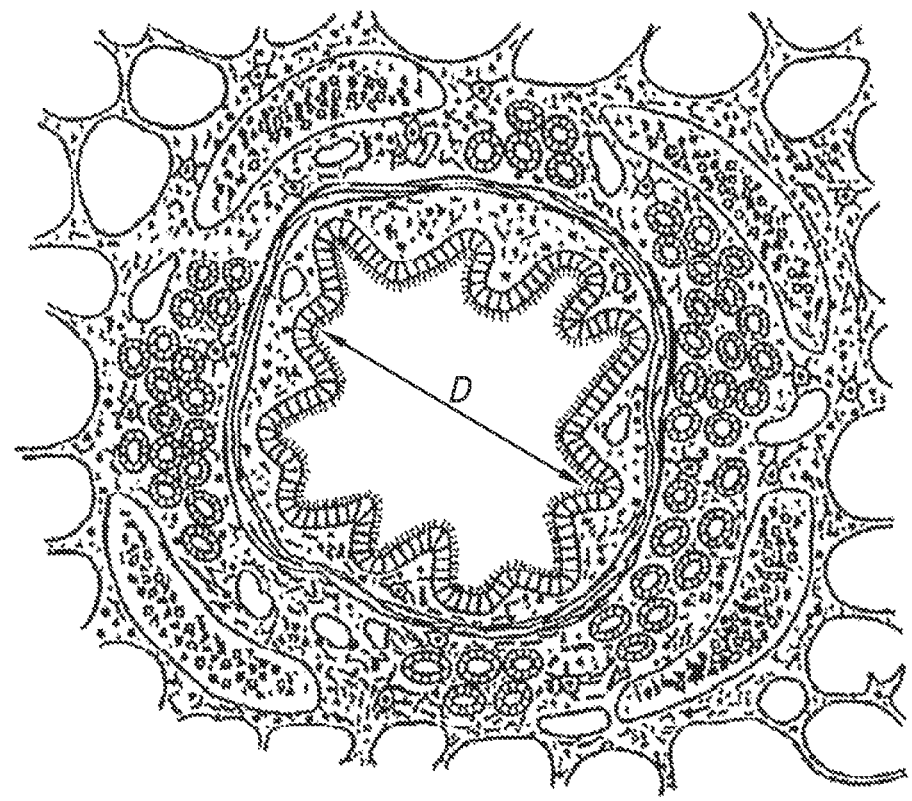
FIG. 1 shows the cross-section of a bronchus.

FIG. 1 shows a cross-sectional view of a bronchus, with a number of its features labeled for reference. The open inner channel (having diameter labeled as D in the Figure) forms the pathway for air to travel from a person's mouth or nose to the lungs. As can be seen, the walls of the bronchus include a number of components, such as the epithelium, blood vessels, smooth muscle tissue, mucous glands, nerve fibers, stroma and cartilage. The nerves or nerve components to be treated through the present invention are located towards the outer surface of the bronchial wall (e.g., away from its open inner channel).

Figure 2:
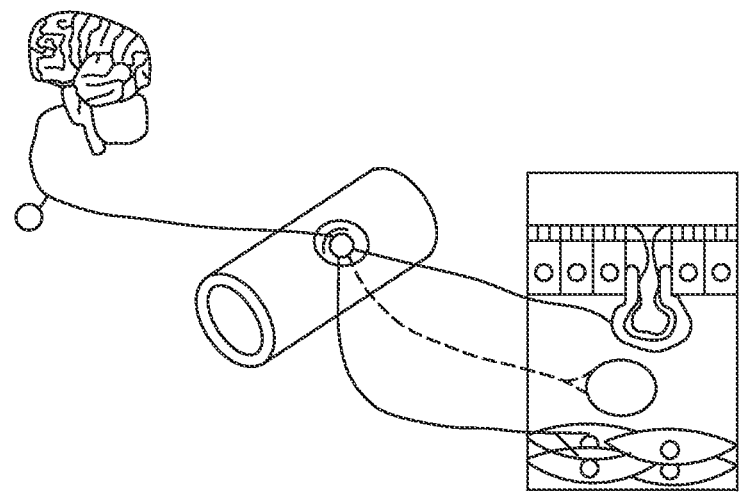
FIG. 2 is a depiction of the autonomic nervous system as it affects the bronchi.

FIG. 2 is a depiction of the autonomic nervous system as it controls the pulmonary system of a person. Extending from the brain is the Vagus nerve, which synapses with parasympathetic ganglion on the bronchi surface. There is a series of parasympathetic nerve components forming a parasympathetic ganglion on the surface of the bronchi, which include post-ganglionic fibers.

The present invention seeks to treat the undesirable and dangerous constriction of muscles of the bronchi that may occur in patients with asthma or chronic bronchitis by disruption, ablation or severing of at least one bronchial nerve component. As used herein, a nerve component is any portion of a nerve that is sought to be treated, and may include a nerve, a ganglion or plexus present on or near the external surface of the bronchi. Most desirably, the nerve component to be treated is a plexus, and particularly the plexus located around the periphery of one bronchi. Since there is more than one nerve component surrounding the outer surface of a bronchi, the treatment may include application of energy around a region of the surface of the bronchi, and may include treatment to a region completely covering a circumference of a bronchi. The treatment may include application of energy to one nerve, multiple nerve components, or all nerve components around a circumference of a region of a bronchi.

As used herein, the terms "proximal" and "distal" are used with reference to a clinician manipulating one end of an instrument used to treat the bronchial diseases. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the drawings. However, surgical instruments may be used in many orientations and positions, and these terms are not intended to be limiting and absolute.

As will be discussed below, the invention provides a method and apparatus for treatment of asthma and other related respiratory disorders, e.g., chronic bronchitis. The apparatus includes an elongated device, having a proximal end and a distal end, where there is an end effector located at or near the distal end of the elongated device. The end effector is designed to provide energy to a surface in which it is in contact, such as the outer surface of the bronchi. The proximal end may optionally include a handle or other control means, as will be discussed below. The inventive energy-providing device is intended to be inserted into the body of the patient such that the end effector is in contact with the outer surface of the bronchi, allowing the end effector to contact one or more bronchial nerves and apply energy to the one or more bronchial nerves. This energy may be sufficient to ablate, disrupt, achieve cell necrosis, or simply sever the bronchial nerves.

Nerves are sensitive to heat and mechanical vibration, so various energy types may be used to achieve the desired result. For example, application of heat through a heated element, such as a heated tip or instrument, or use of a bladder filled with heated fluid may be used. In addition, mechanical vibration such as ultrasonic energy or radiofrequency energy may be used to provide the desired result. Radiation, such as infrared, microwave, or other levels of radiant energy may also be used. In general, any desired energy type may be applied to the surface of at least one nerve, ganglion or plexus. Non-limiting types of energy to be applied include heated elements or electrodes, heated fluid such as gas or liquid, ultrasonic energy, including low-energy ultrasound or high intensity focused ultrasound (HIFU), harmonic energy, direct current (DC) or cauterization exposure, electromagnetic energy, radiofrequency energy, microwaves, plasma energy, infrared, non-ionizing optical energy such as laser treatment, including pulsed laser, fractional laser, or high-energy laser exposure, other radiation energy including alpha, beta, gamma, x-ray, proton, neutron, or ionic radiation. The temperature level applied to the nerve component to be treated should be such that the nerve component is treated but that adjacent tissue is not damaged, or at least that the damage level is minimized. In some embodiments, the energy that is applied by the end effector is sufficient to heat the nerve to about 65° C. The energy application methods may alternatively include exposure to cold temperatures, such as cryosurgical methods. Energy may also include simple mechanical energy such as the use of a blade or blades positioned on or near the end effectors to cut the nerve or nerves. Targeted application of energy effectively treats the nerves, ganglions or plexuses with minimal damage to other structures such as vessels, tissue, muscles, or mucosa.

In some embodiments, the methods of treatment included herein may include the introduction or deposition of certain materials to the target area, including, for example, neurotoxins or other similar nerve-damaging materials. One such material that can be delivered to the target nerve component is onabotulinumtoxinA (commonly known as BOTOX®). Through the use of controlled delivery means such as those described herein for the delivery of energy, delivery of such neurotoxins can be useful in treating the intended nerve component(s). Delivery of such materials can be achieved through use of devices and methods described herein.

The present invention and methods of controlled application of energy to the outer surface of the bronchi, applying targeted energy to the nerve, ganglion, or plexus desired provides a number of benefits to the user. First and foremost, the application of energy is highly targeted and precise due to the visual ability of users to view the instruments and nerves on the bronchi through thoracoscopic means as opposed to the lack of visual ability through the use of bronchoscopic methods. Further, due to the ability to apply energy directly to the desired nerve segment, as opposed to traveling through the bronchi and its various branches and then having to deliver the energy across different tissue layers within the bronchial wall (mucosa, muscle, etc.), there is much less collateral damage to other tissues and bodily components. This provides for a much quicker and less painful recovery process.

The present invention provides an apparatus and method that can treat pulmonary conditions through contacting the exterior surface of the bronchi, as opposed to previously used methods that insert an apparatus through the patient's airway. As such, the inventive methods may be performed through the use of novel thoracoscopic devices adapted to engage the exterior bronchial wall. In such methods, at least one elongated device is inserted through the chest of the patient, and more particularly through a pair of the patient's ribs or in a notch above the sternum. In some embodiments, the apparatus to be inserted may be inserted through a trocar, while in other embodiments, the device may be inserted into the patient's body without the use of a trocar other loading device. The thoracoscopic methods used herein may include the insertion of multiple elongated devices, and may incorporate the techniques known as video assisted thoracoscopic surgery (VATS) or mediastinoscopy. The use of such thoracoscopic methods allows for a user or users to be able to visually see the interior of the patient's thoracic cavity, giving a significantly more targeted and precise surgical technique. As explained above, this allows a user to apply energy or other agents to the nerves, ganglion or plexus around the outside of the bronchi. More than one elongated device may be inserted into the patient during the procedure, including the inventive device having an energy-providing end effector, a camera, atraumatic retractors to help move and/or manipulate lungs, and other devices that may help with identification of the nerve to be treated.

In a VATS technique, each device to be inserted may have an elongated profile with a length and diameter suitable to meet the needs of its use. For example, the method may incorporate the use of an endoscope. Depending on its use and medical discipline, an endoscope may be between 4 cm and 200 cm long. Endoscopes may be rigid or flexible and may have a diameter of from about 2 millimeters to about 15 millimeters, and more particularly about 3-5 millimeters. The elongated devices should have a small enough diameter so as to be insertable through the patient's ribs or chest wall, and to prevent significant trauma to the nerves that travel along the bottom edge of each rib. In addition, each device may have enough flexibility so as to allow maximum mobility inside the chest without putting pressure on the ribs. Thoracosurgical methods allow for smaller incisions into the patient's body, which results in reduced postoperative pain, speed recovery, and provide a superior cosmetic result.

With the patient sedated or anesthetized, and lying comfortably on his or her side, a small incision may be made near the tip of the scapula, or wing bone, on the back. Into this incision, an elongated device may be inserted. For example, a catheter or trocar may be inserted, into which the inventive energy-providing device may be inserted, or alternatively, an introducer may be placed into the chest cavity and air may be introduced into the space around the lung. Although not required, by introducing air, the space around the lung is enlarged, making the lung smaller and allowing for easier treatment. As the lung becomes smaller inside the chest, the surgeon can see more of the structures on and around the lung, including the bronchi. When an adequate space has developed, a small incision is made below the armpit of the patient, and device may be placed into the patient's body. In addition, another incision may be made on the lower chest wall in order to insert surgical devices and/or a drain into the body of a patient. The use of multiple incisions and insertion of multiple elongated devices allows for proper treatment and gives sufficient vision to the surgeon(s) treating the patient. In one embodiment, an endoscope may be inserted through a port near the tip of the scapula, allowing the surgeon to see the apex of the lung. A grasper may be inserted below the armpit, to grasp the apex of the lung. The inventive energy-providing device may be inserted into any desired incision point that gives access to the desired nerve plexus. As noted above, any of the devices may be used and inserted into any desired location on the body, including through a notch formed above the sternum, between ribs, into the back or shoulder, or through any other bodily location.

The location, number, and size of small incisions may vary, which depends upon the number of devices to be inserted into the body of the patient.

The energy-applying device of the present invention may take various shapes and configurations. In some embodiments, the device may include an end effector that has a semi-circular configuration designed to contact the outer surface of a bronchus within its semi-circular opening. In some embodiments, the end effector may include two end components that are movable with respect to each other so as to contact the outer surface of the bronchi therebetween. Such configurations may, for example, include two opposing c-shaped ends, which are each articulatable about a hinge and come together to form a circular or elliptical opening. In other embodiments, the device's end may be pliable or deformable so as to wrap about the outer surface of the bronchi, such as in a helical or other configuration, whereby the surface of the wrapped end contacts the outer surface of the bronchi. In any embodiment, at least a portion of the end effector of the device is in substantial contact with the outer surface of the bronchi and is capable of delivering energy to the surface of the bronchi and, in turn, to the nerve component(s) to be treated thereon. In some embodiments, the device has articulation means located at at least one location along its shaft to facilitate reaching the targeted nerve or ganglion on the bronchi. For example, the device may include a region or regions allowing for rotation and/or articulation, as will be described below.

Figure 3:
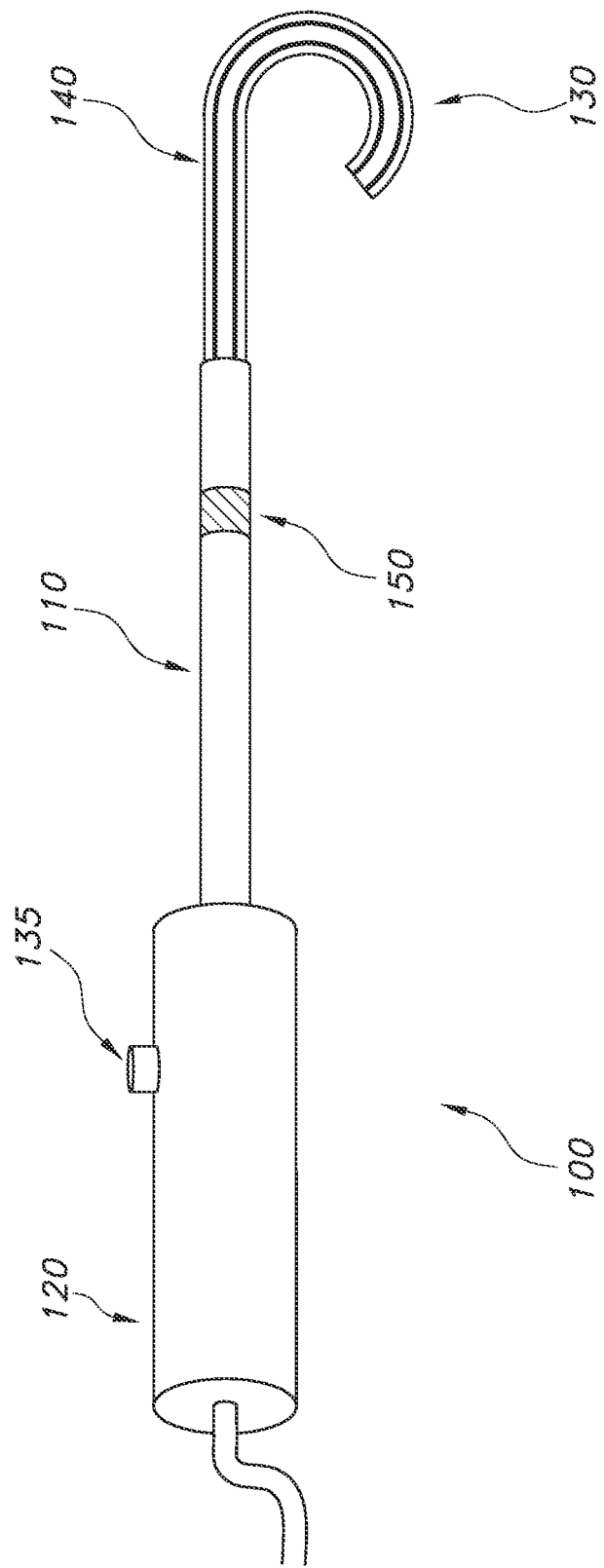
FIG. 3 is a depiction of one embodiment of an energy-applying apparatus of the invention.

With reference to FIG. 3, one embodiment of an energy-applying device of the present invention is depicted. As can be seen, the device 100 includes an elongated shaft 110, which may have any cross-sectional configuration, including a circular or elliptical cross-section. The shaft 110 extends for any desired length, but preferably between 0.5 and 2 feet long, from a proximal end 120 to distal end 130. The length of the shaft 110 should be sufficient to allow for insertion of the distal end 130 into the body of a patient so as to contact the targeted nerve on a bronchi, while still leaving a sufficient length of the shaft outside of the patient's body for control and manipulation by the clinician. The distal end 130 of the device 100 includes an end effector 140, which will be described in greater detail below. The device 100 may include a region 150 or multiple regions along the shaft 110 which may articulate or rotate, if desired. Further, the shaft 110 may be substantially rigid in a curved or straight configuration. In one embodiment, at least a portion of the shaft 110 may be flexible. In this embodiment, the end effector 140 has at least one electrode associated in or on the end effector that is coupled through the shaft 110 and out the handle 125 of the device 100 to a power supply (not shown). The device may include an on-off switch or button 135, or it may include other means of powering on and off the device, if desired.

The shaft 110 of the device 100 may also be configured and sized to permit passage through the working lumen of a commercially available endoscope. However, the device may also be advanced into the body without an endoscope in a minimally invasive procedure or in an open surgical procedure, and with or without the guidance of various vision or imaging systems.

Figure 4A:
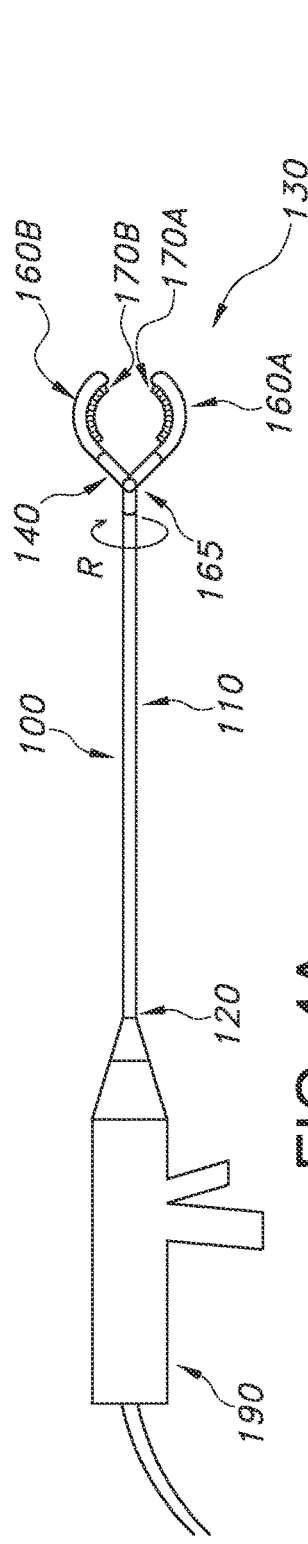
FIGS. 4A, 4B and 4C are alternate embodiments of an energy-applying apparatus of the invention.
Figure 4B:
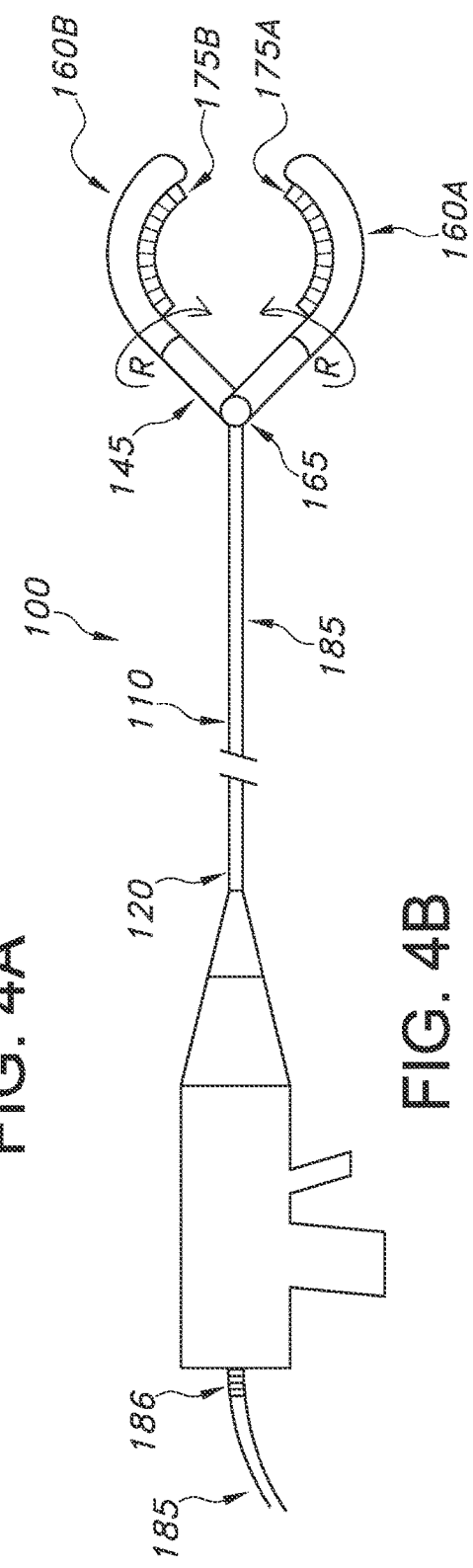

FIGS. 4A and 4B show two different embodiments of end effectors (end effector 140 in FIG. 4A, end effector 145 in FIG. 4B), depending upon the type of energy used to treat the targeted nerve on the surface of the bronchi. It will be appreciated that these embodiments are two possible shapes, sizes, and types, and that alternate shapes, sizes and configurations are within the scope of the present invention. In one embodiment, the end effectors may be rotatable about the point R, such as seen in the various embodiments depicted in FIGS. 4A and 4B. For example, as seen in FIG. 4A, the end effector itself may be rotatable about the point R, and in FIG. 4B, the individual contact components may be independently rotatable.

The device 100 includes a shaft 110 and an end effector 140 (or end effector 145 in FIG. 4B) at its distal end 130, In both FIGS. 4A and 4B, the end effector 140, 145 includes a first contact component 160A and second contact component 160B, which are depicted as being substantially C-shaped or semi-circular components, but other shapes and configurations may be used. The first and second contact components 160A and 160B are movable with respect to each other and capable of being compressed such that they form a substantially circular or elliptical shape. In one embodiment, one of the first or second contact components is fixed with respect to the shaft 110 and the other contact component is movable with respect to the shaft or the other contact component. The device 100 may include a hinge 165, for example, which allows the contact components 160A or 160B to be articulated with respect to each other. It will be noted that when the two contact components 160A and 160B are moved toward each other, they form an open interior into which a bodily lumen, such as bronchi, can be engaged. Each contact component 160A and 160B includes a contact surface, which is intended to substantially contact the outer surface of the bronchi for treatment of the nerve component(s) thereon.

In some embodiments, the energy-applying devices described herein may utilize electrodes to provide electrical energy to the nerve component(s) to be treated. In electrical-energy-applying devices, the end effector may include a series of electrodes having an electrically conductive portion (e.g., medical grade stainless steel) and may be coupled to an energy source. The device may include sharpened edges that contact the outer surface of the bronchi and, more particularly, contact one or more nerve component to be treated. These sharp edges may be configured to deliver a hot cut when energy, such as radiofrequency energy, is applied.

Once the electrodes are positioned proximal to the treatment region, an energizing potential is applied to the electrodes to deliver electric current to the treatment region to treat the nerve components. The electric current may be supplied by an external energy source having a control unit or generator. Energy sources such as those described in U.S. Pat. No. 7,200,445, the content of which is incorporated herein in its entirety, may be used. The energizing potential (and the resulting electric current) may be characterized by a particular waveform in terms of frequency, amplitude, pulse width, and polarity. The electrode may be configured as either an anode (+) or a cathode (−) or may comprise a plurality of electrodes with at least one configured as an anode (+) and the at least one another one configured as the cathode (−). Regardless of the initial configuration, the polarity of the electrodes may be reversed by reversing the polarity of the output of the energy source. The electrodes may be energized with DC voltages and conduct currents at various frequencies, amplitudes, pulse widths, and polarities. The electrodes also may be energized with time-varying voltages and currents at amplitudes and frequencies suitable for rendering the desired therapy. A suitable energy source may comprise an electrical waveform generator adapted to deliver DC and/or time-varying energizing potentials characterized by frequency, amplitude, pulse width, and/or polarity to the electrodes. The electric current flows between the electrodes and through the target nerve component(s) proportionally to the potential (e.g., voltage) applied to the electrodes. In one embodiment, the energy source may comprise a wireless transmitter to deliver energy to the electrodes via one or more antennas.

In one embodiment, the energy source may be configured to produce pulsed or cyclical electrical signals to electrically treat nerve component(s) with the energy-applying device. In one embodiment, a timing circuit may be used to interrupt the output of the energy source and generate a pulsed output signal. The timing circuit may comprise one or more suitable switching elements to produce the pulsed output signal. For example, the energy source may produce a series of n pulses (where n is any integer) suitable to treat the nerve component(s) when the pulsed energy is applied to the electrodes in the end effector. The pulses may have a fixed or variable pulse width and may be delivered at any suitable frequency.

In one embodiment, the energy source may be configured to produce electrical output waveforms at predetermined frequencies, amplitudes, polarities, and/or pulse widths to electrically treat the nerve component(s) with the energy-applying device. When the electrical output waveforms are applied to the electrodes, the resulting electric potentials cause currents to flow through the distal end of the device (at end effector) to treat nerve component(s).

In one embodiment, the energy source may be configured to produce radio frequency (RF) waveforms at predetermined frequencies, amplitudes, polarities, and pulse widths to electrically treat nerve component(s) with the energy-applying device. The energy source may comprise a commercially available conventional, bipolar/monopolar electrosurgical RF generator such as Model Number ICC 350, available from Erbe, GmbH.

In FIG. 4A, the end effector 140 includes electrical contact surfaces 170A and 170B. A first contact surface 170A is located on the interior surface of first contact component (160A). A second contact surface 170B is located on the interior surface of second contact component (160B). The size of the contact surface may be modified to allow for the desired amount of contact with the bronchial wall. In one embodiment, the electrical contact surfaces 170A and 170B are electrodes of opposite polarity so that bipolar RE energy can be delivered to the target nerve or ganglion. In one embodiment, the electrical contact surfaces 170A and 170B are electrodes of similar polarity, i.e., they form an active electrode. A return electrode in the form of a grounding pad placed on the surface of the patients skin is coupled to the power supply so that monopolar RF energy can be applied to the targeted nerve or ganglion. In one embodiment, the electrical contact surfaces 170A and 170B are resistive elements that enable resistive heating of the targeted nerve or ganglion.

In FIG. 4B, an end effector 145 includes bladder contact surfaces 175A and 175B into which heated fluid such as water, air, or other liquid or gas may be introduced. In this figure, both surfaces 175A and 175B are bladder contact surfaces, but it is understood that it may be useful if only one surface is a bladder contact surface, and the other surface is not a bladder surface. Introduction of heated media such as gas, water, steam, or oil is accomplished by way of conduits which are fluidly coupled from the bladder to a source of heated media coupled to the proximal end of the device. In one embodiment, coupling and delivery of fluid or other media is accomplished by connection of the bladder contact surfaces 175A and 175B with a tube 185 housed within the shaft 110 of the device, the tube 185 ending at a port 186 on the proximal end of the device. The port 186 can be in the form of a luer lock fitting or other quick connect means known to those skilled in the art of coupling fluids through tubes and other compartments. The size of the contact surfaces 175A and 175B may be modified to allow for the desired amount of contact with the bronchial wall. In an embodiment including bladder contact surface(s), at least one opening is present on the surface of the bladder contacting surfaces 175A and 175B to allow for elution of neurotoxins from the contacting surfaces. A source of neurotoxin is coupled to the proximal end of the device and the toxin can be injected through the tube and into the bladder where it can leave the bladder and treat the targeted nerve or ganglion.

Figure 4C:
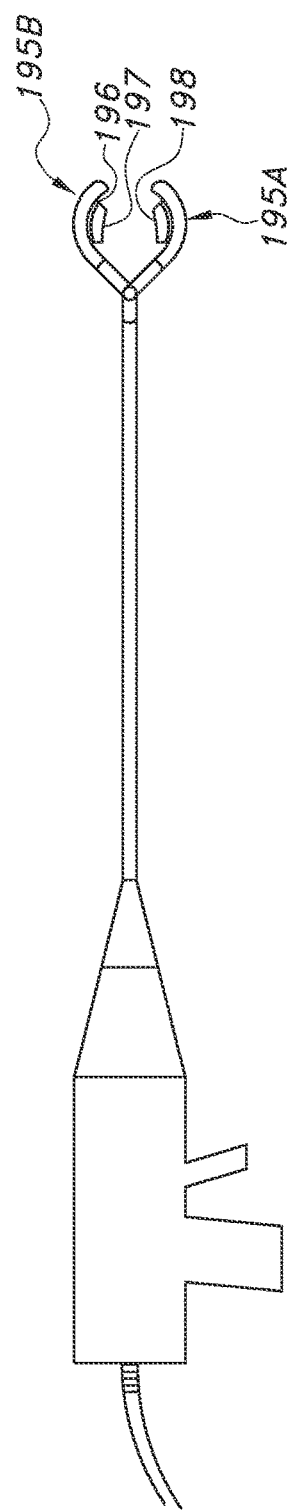

FIG. 4C illustrates another embodiment of the present invention in which contact surfaces 195A and 195B include at least one blade 197 capable of transecting the nerve targeted for treatment. In one embodiment the blades are embedded in a rigid polymeric backing 196. The blade or blades 197 may be made of any material, including, for example, stainless steel. The blade or blades 197 may have a height, relative to the surface of the polymer backing, of between 1 and 3 mm. The opposing surface may include an anvil 198 or other component against which the blade 197 may contact, and may include a second blade or blades if desired.

The device 100 may optionally include a handle 190 or other control means at its proximal end 120, which may include a control mechanism to manipulate the device 100 and the end effector 140. For example, a trigger may be provided that is coupled to a ratcheting mechanism or cable driven mechanism to move one or more contact components 160A or 160B with respect to each other once in place or may include mechanisms to wrap the end effector about the bronchi. Wires 195 may extend through the proximal end 120 and optionally through the handle 190 so as to provide energy to the end effector 140. A power supply is not shown but known power supply sources may be used in the present invention including those described in U.S. Pat. No. 7,200,445, incorporated by reference above. In one embodiment, the power supply includes an energy generator, a controller coupled to the energy generator, and a user interface surface in communication with the controller. Although variations of the device shall be described as RF energy delivery devices, variations of the device may include resistive heating systems, infrared heating elements, microwave energy systems, focused ultrasound, cryoablation, or any other energy delivery system. Additionally, the device may include a connector common to such energy delivery devices. The connector may be integral to the end of a cable as shown, or the connector may be fitted to receive a separate cable. In any case, the device may be configured for attachment to the power supply via some type connector. The power supply may have connections for the device, return electrode (if the system employs a monopolar RF configuration), and optionally an actuation pedal(s). The power supply and controller may also be configured to deliver RF energy to an end effector having electrodes configured for bipolar RF energy delivery. The user interface may also include visual prompts for user feedback regarding setup or operation of the system. The user interface may also employ graphical representations of components of the system, audio tone generators, as well as other features to assist the user with system use. A wireless energy supply may be provided through the use of one or more antennas in the device 100 or an internal energy supply source may be used.

Referring again to FIGS. 4A-4C, the end effector 140 may include only one contact component 160A and may have only one contact surface 170A (or 175A, for example). The end effector 140 may have a substantially C-shaped or semi-circular contact component 160A, or it may have any desired shape.

The end effector 140 may be collapsible, so as to provide the device 100 with a narrow profile and therefore aid in insertion of the device through a trocar and into the body of the patient. For example, the end effector 140 may be spring-loaded, such that it may be compressed when the distal end 130 is inserted into a trocar, and may spring open when it exits through the distal end of the trocar. Conversely, the end effector may collapse when being pulled back through the trocar and then expand again upon exiting the patient. In one embodiment, one or both of the end effectors may include a shape memory alloy, such as nitinol. The end effectors could then have a first configuration and a second configuration.

The contact surfaces 170A and 170B illustrated in FIG. 4A or 175A and 175B in FIG. 4B may include a soft or pliable surface, if desired. The use of a soft or pliable surface may be useful in protecting against unintentional squeezing or crushing of the bronchi within the interior of the end effector 140. Thus, the contact surface of end effector may be configured to have an atraumatic engagement with the bronchi and simultaneously ensure sufficient energy is applied to the nerve components to be treated. As noted above, the device 100 may be inserted into the body of a patient and manipulated by the surgeon so that the bronchi are aligned between the contact surfaces 170A and 170B of FIG. 4A or 175A and 175B in FIG. 4B.

In one embodiment, the device may include a means for feedback, such as tactile or haptic feedback, when in use. For example, although the device is intended to be used in concert with other endoscopic instruments such as an endoscope with a light source and camera, the device may give some sensation in the form of feedback when an object is contacted by one or more surfaces 170A or 170B. Using a feedback system may allow for controlled closure of the end effector 140 and protect against undesired crushing or collapsing of the bronchi disposed therein.

Figure 5:
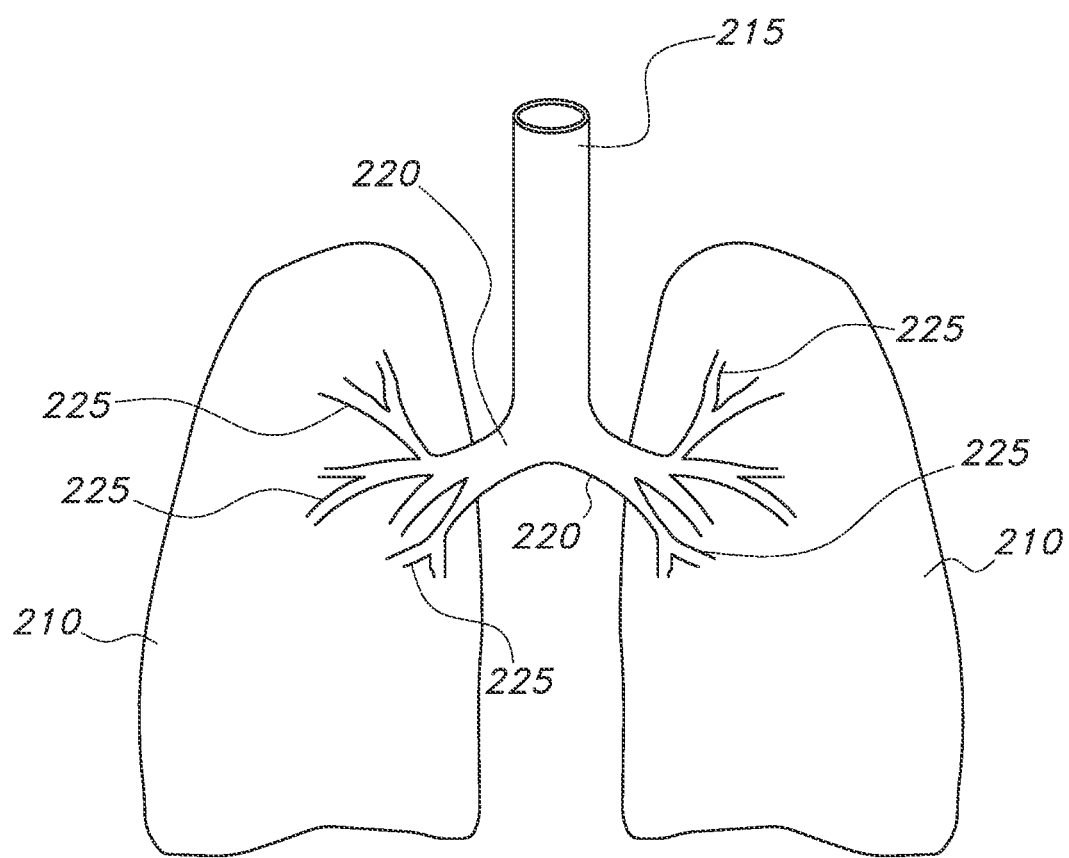
FIG. 5 is a depiction of the pulmonary system of a human.
Figure 6:
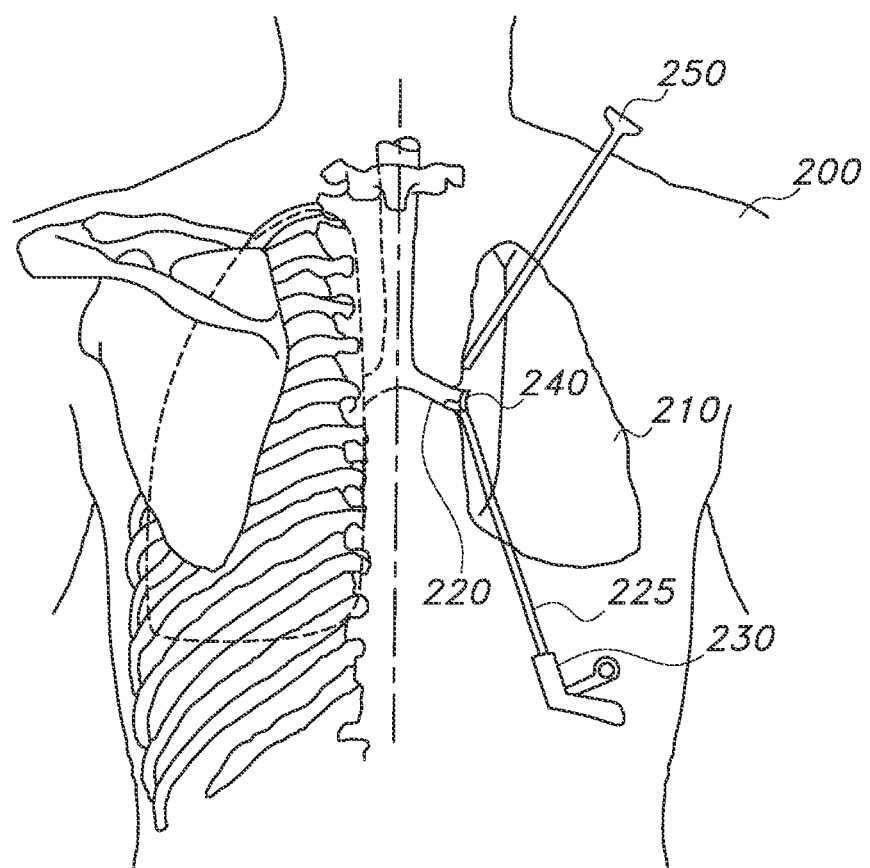
FIG. 6 is a depiction of a surgical procedure using the energy-applying apparatus of the invention.

FIGS. 5 and 6 show the pulmonary system of an individual and an example of the surgical procedure useful herein, respectively. The system includes the lungs 210, trachea 215, mainstem or primary bronchi 220, and secondary bronchi 225. The trachea divides into the two primary bronchi at the level of the sternal angle and of the fifth thoracic vertebra or up to two vertebrae higher or lower, depending on breathing, at the anatomical point the carina of trachea. The right main bronchus is wider, shorter, and more vertical than the left main bronchus. It enters the right lung at approximately the fifth thoracic vertebra. The right main bronchus subdivides into three secondary bronchi which deliver air to the three lobes of the right lung: the superior, middle and inferior lobe. The left main bronchus is smaller in caliber but longer than the right, being approximately 5 cm long. It enters the root of the left lung opposite the sixth thoracic vertebra.

The present invention is useful for treatment, including to treat nerves or ganglion that exist on the either or both of the mainstem bronchi 220. As noted above, the surface of the bronchi 220 includes a number of components, including nerves and the nerve components to be treated through the present invention. FIG. 6 illustrates the body of a patient 200, showing the left lung 210 and its mainstem or primary bronchus 220. A number of instruments may be partially inserted into the body 200 of the patient, and in the depiction shown in FIG. 6, two elongated instruments are inserted. One is the shaft 225 of the inventive device 230, having end effector 240, and the other is a manipulation device 250, which may be used to physically move and manipulate portions of the lung 210 during the procedure. In one embodiment, the device is used in concert with an endoscope having a light source and camera (not shown). The inventive device 230 is inserted into the patient's body by the methods described herein, such that the end effector 240 is substantially in contact with the primary bronchus 220 at a desired location. Once the end effector 240 is in contact with the intended location at the bronchus 220, energy may be applied to the end effector 240, and thus energy is provided to the bronchus 220. Depending on the configuration and design of the end effector, the energy may include electrical energy, radiofrequency energy, direct current energy, mechanical energy, microwave energy, and ultrasonic energy.

Figure 7A:
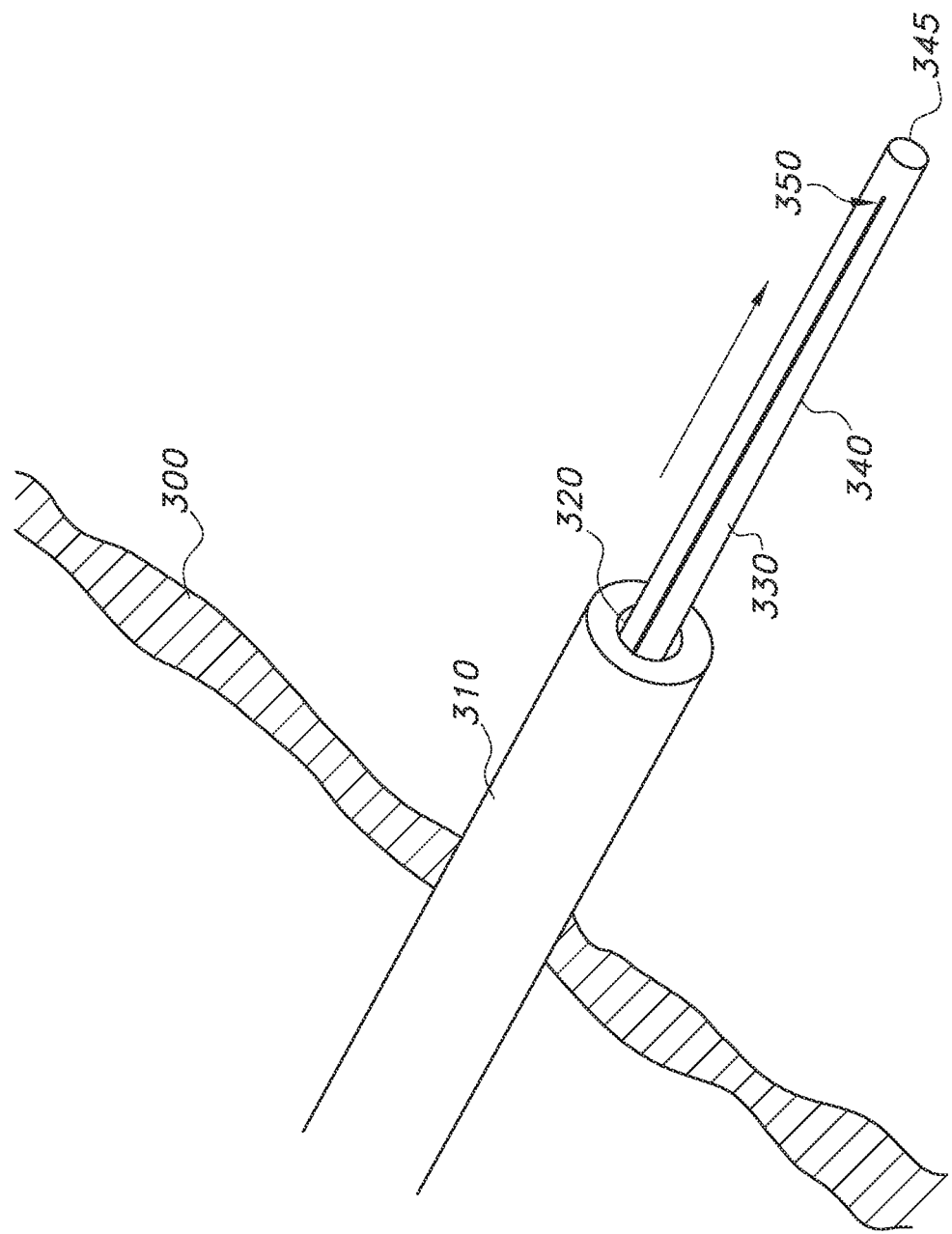
FIGS. 7A-7B show an alternate embodiment of the present invention including a wrappable end effector applying microwave energy to a nerve on an external surface of a bronchus.
Figure 7B:
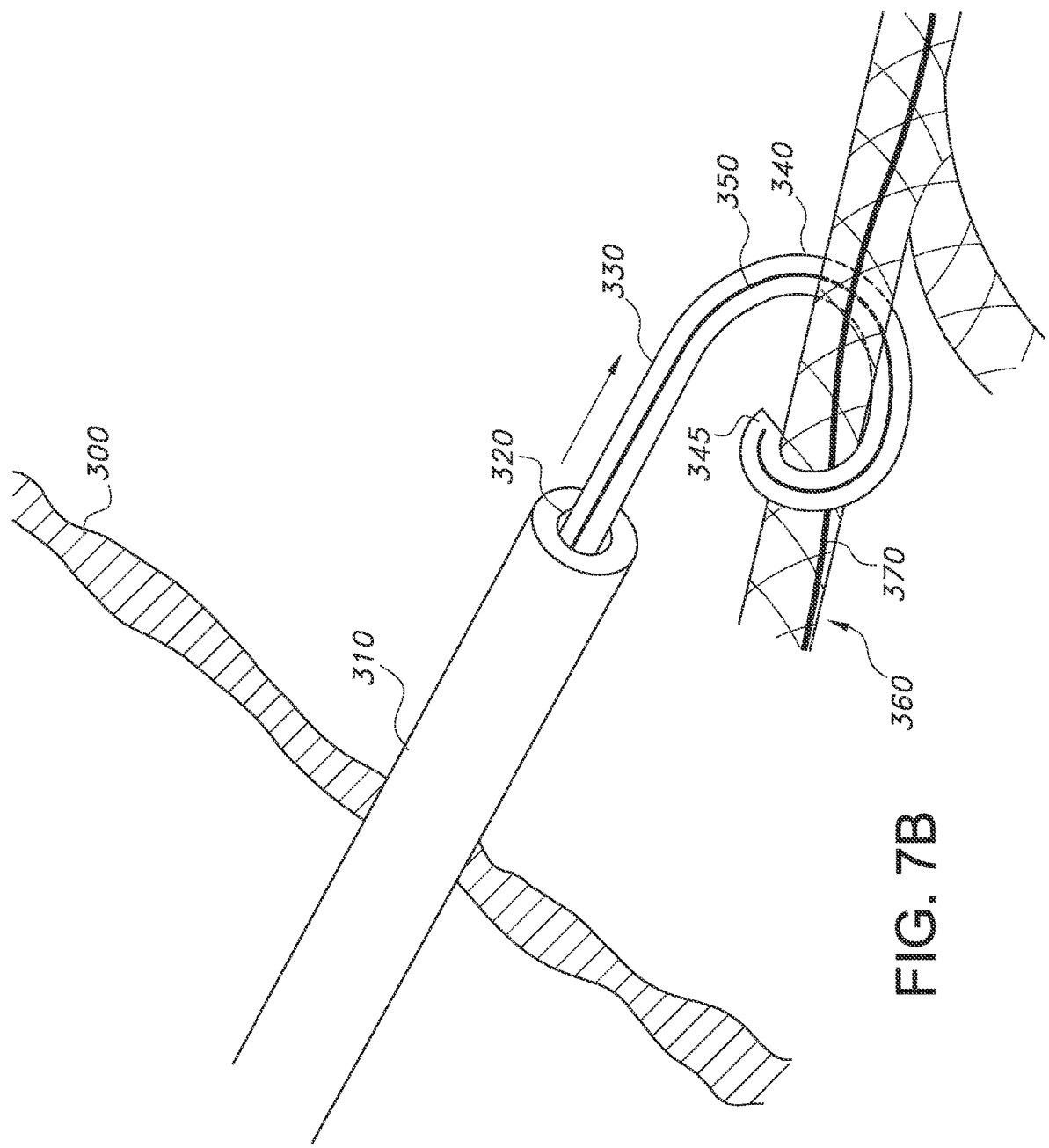
Figure 8:
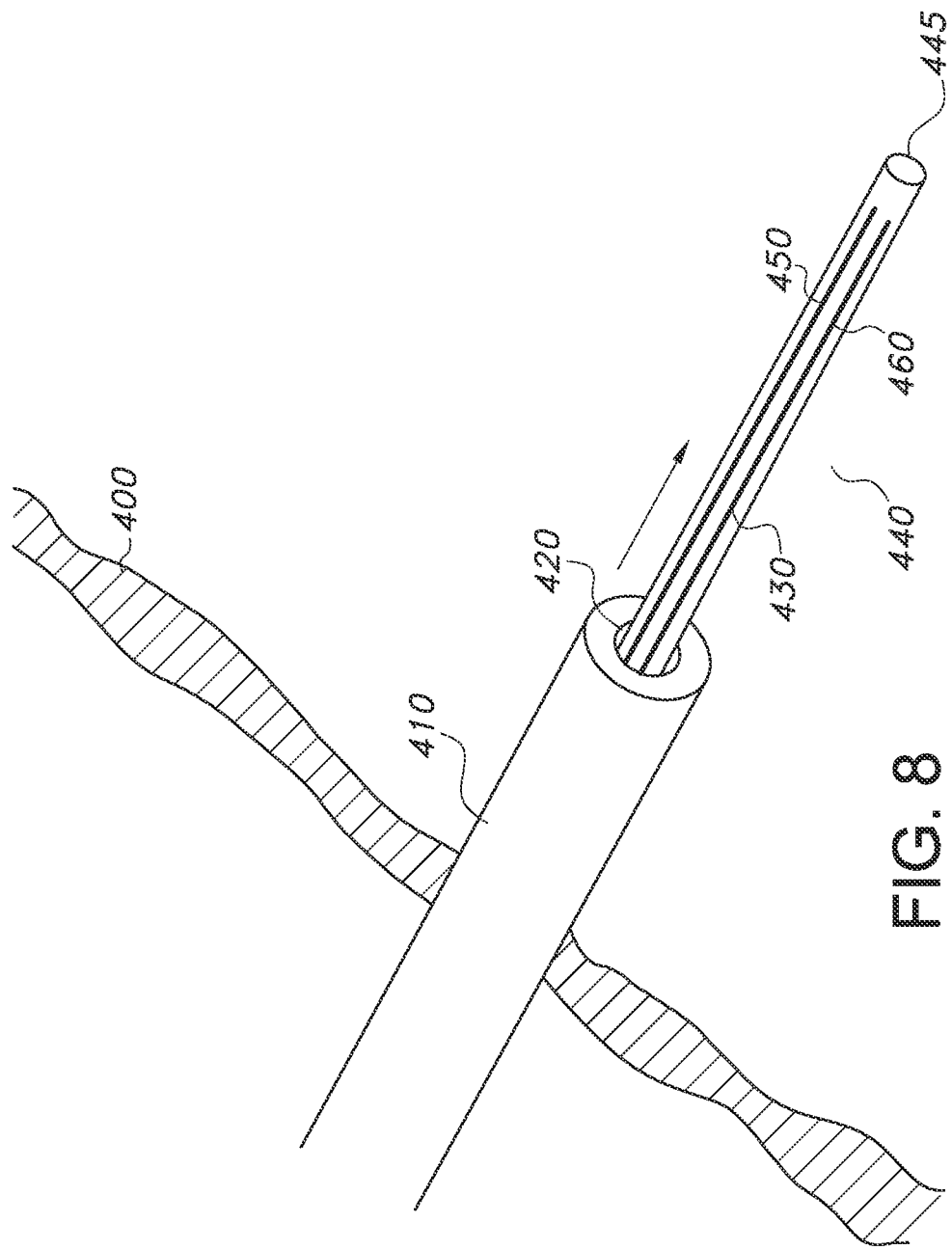
FIGS. 8-8A show an alternate embodiment of the present invention including a wrappable end effector applying radiofrequency energy to a nerve on an external surface of a bronchus.
Figure 8A:
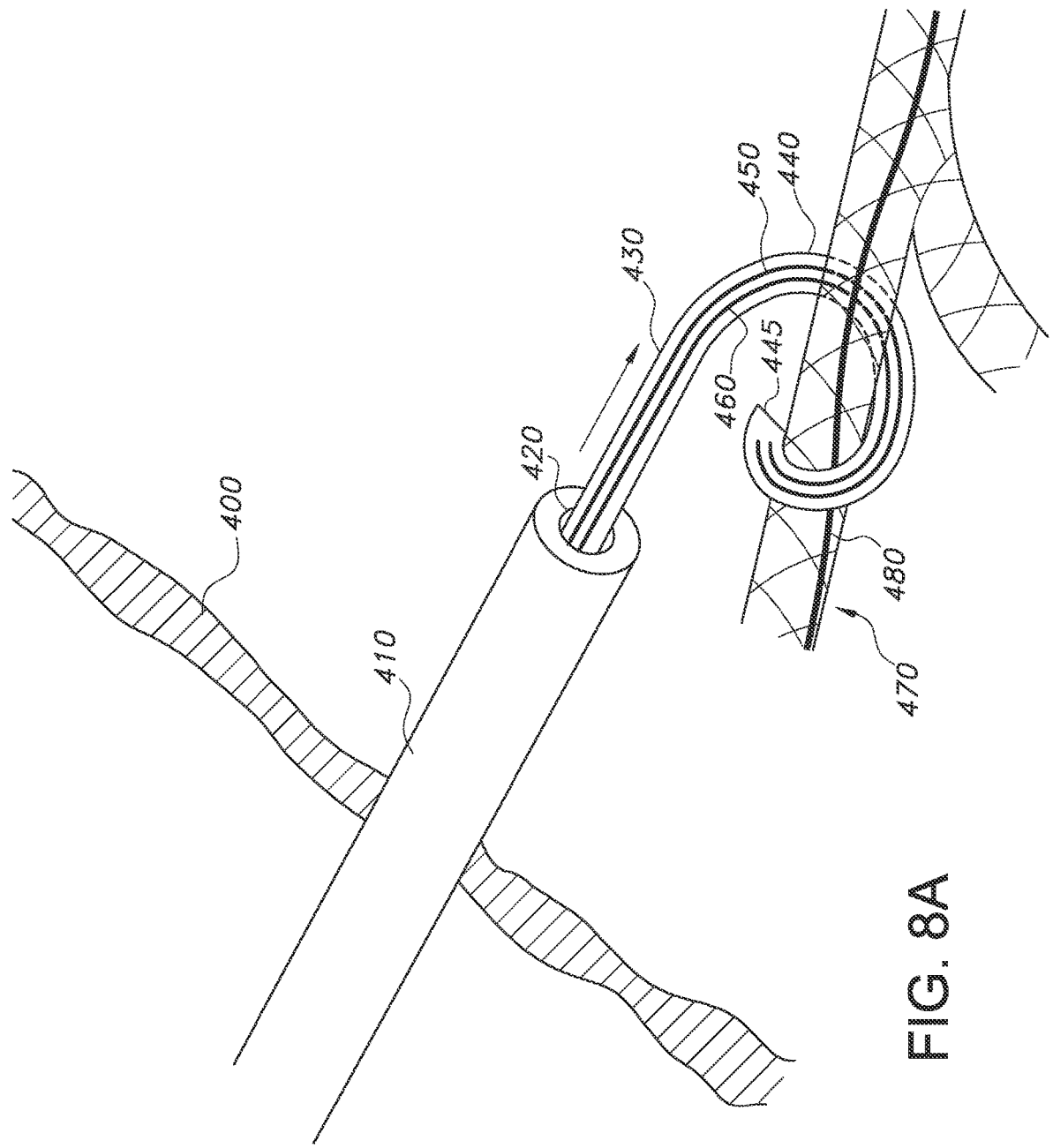

FIGS. 7A, 7B and 8, 8A depict alternate embodiments of the end effector of the present invention, in particular, a wrapping-type end effector. As discussed above, any configuration of device may be used such that the end effector contacts at least a portion of the outer surface of the bronchi to be targeted and more desirably contacts a substantial portion of the circumference of the bronchi. In FIGS. 7B and 8A, an end effector is depicted that wraps around the outer surface of the bronchi, as opposed to being clamped or clasped around the outer surface of the bronchi (as in FIGS. 4A-4B). FIGS. 7A-7B show a wrapping-type end effector using microwave energy, while FIGS. 8-8A show a wrapping type end effector using radiofrequency energy. It is understood that any energy form may be used, and FIGS. 7A, 7B, 8, and 8A only depict two potential energy forms.

Since the introduction of anatomic lung resection by video-assisted thoracoscopic surgery (VATS) was introduced, VATS has experienced major advances in both equipment and technique, introducing a technical challenge in the surgical treatment of both benign and malignant lung disease. The demonstrated safety, decreased morbidity, and equivalent efficacy of this minimally invasive technique have led to the acceptance of VATS as a standard surgical modality. The present invention can be used during VATS to treat the targeted nerves so that symptoms of asthma or chronic bronchitis can be reduced.

FIG. 7A illustrates the chest wall 300 of a patient, into which a loading device 310 (such as catheter, port, or trocar) may be inserted. The loading device 310 has a central lumen 320, into which the elongated energy applying device 330 of the present invention is inserted. Proximate the distal end 345 of the device 330 is the end effector 340 of the device 330. Along a substantial portion of the device 330, and particularly at or near the end effector 340 of the device 330 is a microwave energy emitting device 350. FIG. 7A shows the end effector 340 of the device 330 as it is being pushed or advanced by the surgeon. It exists as a first straightened state while in the lumen of the trocar, and may be capable of curving after it exits the trocar, either through self-curving methods or by enacting force on the device to cause curving. In the embodiment of FIG. 7A, the device remains straight until a force causes curving, but it is understood that the device may automatically begin to curve after it leaves the trocar and force is not acted on it.

In one embodiment, the distal end of the device of FIG. 7A includes flexible and configurable materials, such as nitinol or another deformable material. The deformation should be controllable from external means, such as a proximal handle or by other devices insertable into the body. Control can also be accomplished, in the case of a distal end including nitinol, by simply advancing or retracting the distal end of the device into or out of the lumen in the trocar. The distal end, once outside the trocar and in the patient's thoracic cavity, is free to assume a second configuration. This second configuration may be a curved C shape, a coil, a semi-circle, or a spiral so as to enable the surgeon to place the energy delivering component of the device on the target nerve or ganglion. Further, the end effectors of these embodiments may include means for alerting the clinician when wrapping is achieved, or to warn the clinician when excess or insufficient pressure is exerted on the bronchi. Visual means may be particularly useful in using a wrapping-style of end effector. FIG. 7B illustrates the device 330 in a second state, in which the end effector 340 of the device 330 is at least partially wrapped around the outer surface of a bronchus 360. As can be seen in FIG. 7B, a nerve 370 is disposed along the outer surface of the bronchi 360, and by wrapping the end effector 340 around the bronchi 360, at least a portion of the nerve 370 is in contact with the end effector 340. FIG. 7B shows the end effector 340 wrapped around the bronchi 360 in a helical configuration covering 360 degrees of the outer surface, but it will be understood that the end effector 340 may be disposed in any configuration and may cover any desired portion of the outer surface of the bronchi 360. Once in position as in FIG. 7B, energy may be provided by a power supply described previously herein. In one embodiment, the power supply is comprised of a microwave generator. Thus, the energy emitting component 350 is activated so that the appropriate energy can be applied to the targeted nerve 370 or ganglion on the bronchi.

FIGS. 8 and 8A illustrate one embodiment of the present invention used to apply radiofrequency (RF) energy to a target nerve or ganglion. FIG. 8 illustrates a chest wall 400 of a patient, a loading device 410, which has a central lumen 420, and the energy emitting device 430 of the present invention (terminating in distal end 445). Device 430 and its end effector 440 include an energy source, in this embodiment including first electrode 450 and second electrode 460 of opposite polarity so that bipolar RF energy can be applied across the electrodes and proximate the target nerve or ganglion. In another embodiment, the electrodes are of similar polarity and the return electrode exists as a grounding pad on the patient's skin so that monopolar RE energy can be applied. In either embodiment, as can be seen in FIG. 8A, the end effector 440 is brought into contact with the outer surface of the bronchi 470, where it is in substantial contact with at least a portion of a nerve 480. The end effector 440 may be brought into contact with the outer surface of the bronchi 470 in any configuration or to any extent, such that it contacts at least a portion of the nerve component 480 to be treated. The first and second electrodes 450/460 are powered by a separate energy source, which may be secured to the device 430 by wires or may be an internal source such as a battery located within the handle of the device, or may be wireless transmission of power.

The devices 330 and 430 of FIGS. 7A-7B and 8-8A may be enabled have a predetermined curvature by employing the use of a nitinol shaft (not shown) within the core of the device. The curvature of the nitinol core is predetermined and is constrained while being passed through the trocar. In one embodiment, the nitinol core extends along the entire length of the device. In another embodiment, the shaft of the device may have a smaller diameter metal other than nitinol. This metal core can be bent or deformed into any configuration the surgeon desires so as to customize the curvature, and thus help bring the electrodes in close contact with the nerve or ganglion. In this method of use, a trocar may or may not be used, depending on whether the desired shape of the device's shaft can fit through the trocar. The deformation may be controllable from external means, such as other devices typically used by endoscopic surgeons, endoscopic clamps, forceps, etc. that are insertable into other trocars and then brought into contact with the shaft so as to bend or curve it into the desired configuration that can contact the exterior bronchial wall. Further, the end effectors of these embodiments may include means for alerting the clinician when wrapping is achieved, or to warn the clinician when excess or insufficient pressure is exerted on the bronchi. In some embodiments, the energy applied may be sufficient to cause irreversible electroporation (IRE), which is the process of killing cells by applying large destabilizing electrical potentials across the cell membranes for a long period of time. IRE provides an effective method for destroying cells while avoiding some of the negative complications of heat-inducing therapies. In particular, IRE destroys cells without the use of heat and does not destroy the extracellular matrix. Large destabilizing IRE electric potentials may be in the range of about several hundred to about several thousand volts applied across biological membranes over a distance of about several millimeters, for example, for a relatively long period of time. The destabilizing electric potential forms pores in the cell membrane when the potential across the cell membrane exceeds its dielectric strength causing the cell to die by processes known as apoptosis and/or necrosis.

In one embodiment, irreversible electroporation (IRE) energy may be in the form of bipolar or monopolar pulsed direct current (DC) output signals to electrically treat nerve component(s) with the energy-applying device. The energy source may comprise a commercially available conventional, bipolar or monopolar Pulsed DC generator such as Model Number ECM 830, available from BTX Molecular Delivery Systems Boston, Mass. In bipolar mode a first electrode may be electrically coupled to a first polarity and a second electrode may be electrically coupled to a second (e.g., opposite) polarity. Bipolar or monopolar pulsed DC output signals (e.g., DC pulses) may be produced at a variety of frequencies, amplitudes, pulse widths, and polarities. For example, the energy source may be configured to produce DC pulses at frequencies in the range of about 1 Hz to about 1000 Hz, amplitudes in the range of about +/−100 to about +/−3000 voltage direct current (VDC), and pulse widths (e.g., pulse durations) in the range of about 1 μs to about 100 ms to electrically treat the intended nerve component(s). The polarity of the energy delivered to the electrodes may be reversed during the therapy. For example, the polarity of the DC pulses initially delivered at amplitudes in the range of about +100 to about +3000 VDC may be reversed to amplitudes of about −100 to about −3000 VDC. In some embodiments, the nerve component(s) may be treated with DC pulses at frequencies of about 10 Hz to about 100 Hz, amplitudes in the range of about +700 to about +1500 VDC, and pulse widths of about 10 μ.s to about 50 μ.s.

Once the energy-applying device is positioned such that the end effector is at least partially in contact with the nerve component(s) to be treated, and the electrical connections are completed, the nerve component(s) may be treated with energy supplied by the energy source. As explained above, the energy may include any of the energy forms previously described. Following the application of energy, the energy-applying device may be removed from the patient, however, if subsequent application of energy is necessary to completely treat the nerve component(s) or to treat additional nerve component(s), the energy applying device may be reinserted into the body of the patient, through either the same incision location or through a different incision location. The treated nerve component(s) may be monitored over time (e.g., days, weeks, or months) to observe any follow-on activity.

The energy source, regardless of the type of energy to be applied, may energize the end effector through a wired or a wireless connection. In a wired connection, the energy source is coupled to the end effector by way of one or more electrically conductive wires through the body. In a wireless connection, the energy source may be coupled to the end effector by way of one or more antennas, thus eliminating the need to have a wired connection running through the body of the energy-applying device, or the energy source may be disposed internal of the energy-applying device. In a wireless embodiment, an internal cable may be replaced by an antenna, for example. The antenna may be coupled to the end effector by an electrically conductive wire (not shown).

The end effector may additional include a light-emitting means to assist in targeted and precise delivery of the energy. The end effector may also include a means to provide feedback, such as tactile or haptic feedback, to the user. The feedback may give the user a warning that the device is inserted too shallow or deep, or that the device is in contact with other bodily organs. In addition as the end effector is applied around the circumference of the bronchi, the device may provide feedback that alerts the user to the pressure being applied to the outer surface of the bronchi. In some embodiments, the exact diameter of the bronchi to be treated is known, and the end effector can be set to alert the user when the end effector has reached the intended or desired diameter. The feedback can thus prevent the user from exerting an undesirable level of pressure onto the bronchi.

The device may be capable of providing energy to the target site so as to generate a range of temperatures and, in some embodiments, the method of use may include starting at a lower energy and raising the energy levels to arrive at an increased temperature. In addition, the device may include one or more instruments that are capable of determining the temperature of the treated bronchial surface or the current applied, and may be configured to stop application of energy if necessary. For example, the device may include one or more thermocouples configured to measure the temperature at the site of treatment and protect against overheating. In addition, the device may include a mechanism to cool the target site if needed, for example, through the use of a cooled water jacket or other cooling methods. This is an additional safety or control mechanism that reduces or eliminates the risk for damage to the patient, such as through overheating or uncontrolled temperature application. The device may include or utilize a number of algorithms to adjust energy delivery, to compensate for device failures, to compensate for excess current, to compensate for improper use or insufficient contact, or to compensate for tissue inhomogeneities or variations in the nerve component(s) targeted.

Figure 9:
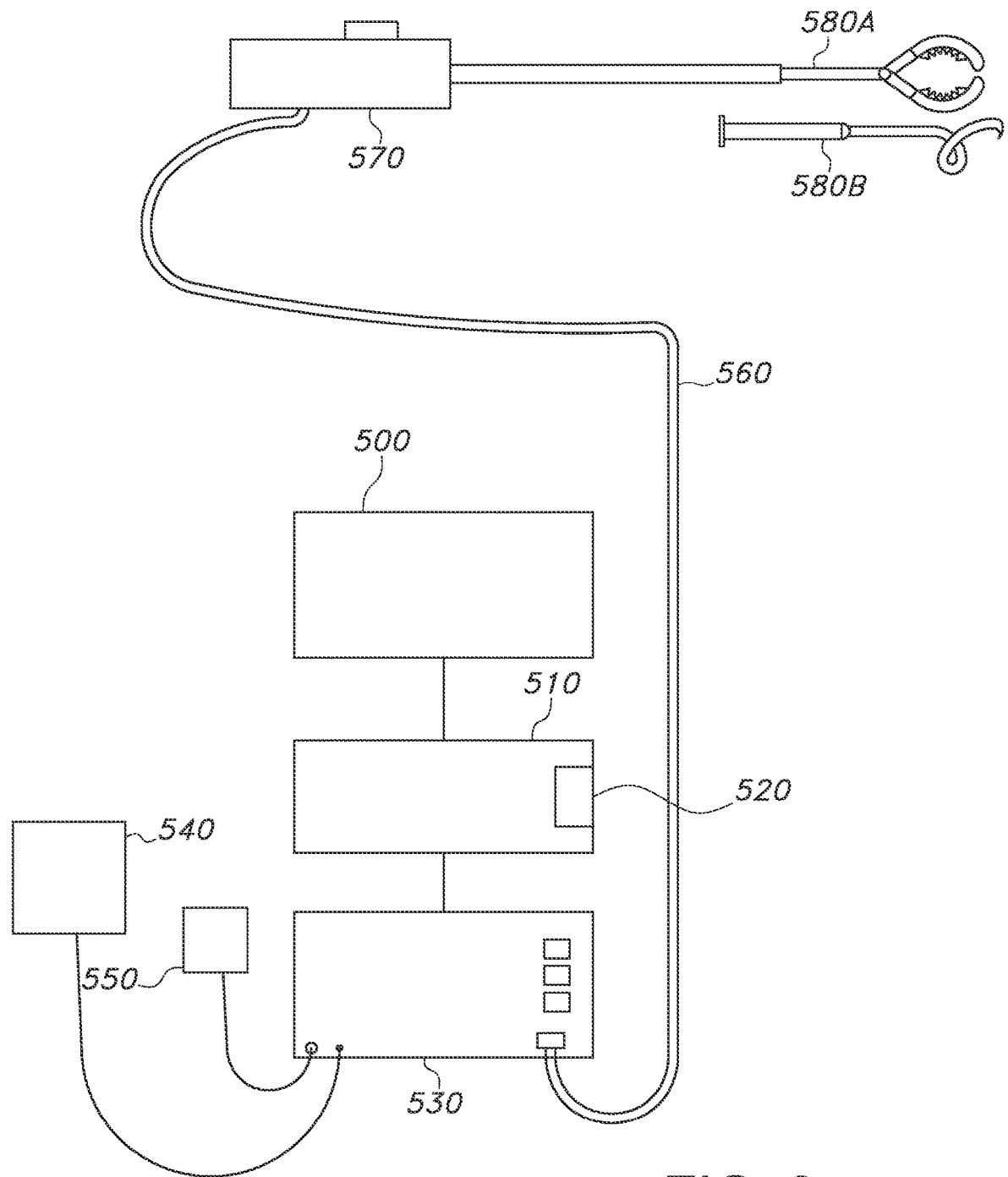
FIG. 9 is an exemplary external powered device useful in the present invention.

A controller and power supply may be used, where the power supply may be internal of the device or may be external and connected to the device, such as through the use of wires or connectors. An exemplary external powered device is seen in FIG. 9, which includes an energy generator 500, a controller 510 (including processor 520), and power supply 530. The power supply 530 should be configured to deliver energy for a sufficient duration and in the manner desired. The power supply 530 may include programmable information such as a timer. The power supply 530 may also employ a number of algorithms to adjust the energy delivery before or during treatment, if desired. Further, the power supply 530 may be capable of monitoring the various parameters of energy transfer, including, for example, voltage, current, power, impedance, and may use this monitored information to control the output. The level of power may be increased or decreased either by a user or automatically in response to one or more monitored levels. A return electrode 540 may be connected to the power supply 530, and optionally an actuator 550 may also be included. The device is connected via appropriate wiring 560 to the device 570, which includes end effectors, such as those described above (e.g., 580A, 580B). In some embodiments, end effectors may be capable of being removed and/or replaced, such as through the use of a modular device. Any engagement means may be used to secure an end effector to the device, including friction fits, snap on-snap off tooling, screw fit, and the like. The invention may include a kit, which contains the body of the device and a plurality of modular end effectors.

The present invention provides methods of controlled and targeted application of energy to a nerve, ganglion or plexus, particularly those located on the outer surface of an individual's bronchi. The invention includes the use of an energy-applying device, such as that described above. In one useful method of application of energy, a user (typically a surgeon) makes at least one small incision into the body of a patient. The incision is located at or near the thoracic position of the patient and in particular should be at a point between two adjacent ribs of the patient. Once the incision is complete, the user inserts the distal end of the energy-applying device into the body of the patient. In some embodiments, a port or trocar may be placed in the incision site. The insertion of the energy-applying device is such that the distal end of the device, which includes an end effector described above, can substantially contact at least a portion of the outer surface of a bronchi.

If desired, additional devices to allow for a VATS technique may be used, including, for example, devices to move or manipulate lungs, lobes of lungs, and bronchi. In addition, video devices may be inserted through additional incision locations in the patient's body. Other tools may be inserted to help visualize the interior of the body, or to help manipulate and/or place the end effector in the proper location.

Once the desired devices are inserted into the body of the patient, the end effector of the energy-applying device is moved into a position at or near one of the bronchi. The end effector is then placed into substantial contact with the outer surface of the desired bronchi, where it contacts at least one nerve component to be treated. The end effector may include a clamp-type effector (such as in FIGS. 4A-4C) or it may include a wrapped end effector (such as in FIGS. 7A-8), or may be any other configuration in which at least a portion of the outer surface of the bronchi is contacted by a contact surface of the end effector. Most desirably, the contact surface of an end effector contacts the bronchi at least a portion of the circumference, preferably 45 degrees to 360 degrees. The end effector is opened such the energy-applying surface of the end effector is positioned so as to contact the outer surface of the bronchi. The nerve component, ganglion or plexus is placed into contact with the energy-applying surface of the end effector and, if desired, the end effector can be closed around at least a portion of the circumference of the bronchi, where the nerve components to be treated are located. Energy may be applied to one or more nerve components simultaneously. Thus, the application of energy may be provided to a small region, including one nerve component, or may be applied to a plurality of regions covering at least a portion of the circumference of bronchi to be treated. In some embodiments, the end effector is disposed around an entire circumference of the bronchi, allowing application of energy to all nerve components disposed in that region of the bronchi. The end effector may have any size desired so as to cover as much or as little of the surface of the bronchi to be treated. Multiple regions may be treated on one bronchi or bronchial segments.

Once the nerve component (ganglion or plexus) to be treated is in contact with at least one energy applying surface of the end effector, the user can introduce energy to the end effector and treat the nerve component to be treated. The energy application is sufficient such that the intended effect is achieved, such as severing or ablation of the nerve component. In some embodiments, the energy applying surface of the end effector may have a conformable surface such that when the end effector is placed into position about the bronchi, there is minimal, if any, compression of the bronchi. In some embodiments, the energy applying surface of the end effector includes at least one blades or sharp edge, and the application of mechanical energy includes severing the nerve component to be treated.

Once the desired energy is applied to the nerve component or components to be treated, the energy applying device may be removed. If other devices such as light sources, cameras, or other endoscopic tools were inserted, they may also be removed. The treated bronchial site may be given additional treatment, including application of drugs or other medication, or may be wrapped or coated with a material to promote healing and/or to restrict regrowth or rejoinder of the severed or ablated nerve components.

As noted above, the present invention uses the application of energy to the exterior surface of the bronchi, giving targeted and precise treatment to one or more of the nerve components located on the exterior surface of the bronchi. This method and apparatus for achieving the method provides a number of benefits over previous methods, the previous methods including, for example, intra-bronchial methods (bronchoscopic methods) and methods that attach or implant a device to the bronchi. The invention provides a method of treating pulmonary conditions through targeted means, giving a less painful recovery and quicker recovery time, while also avoiding the need to implant a device in the body. Further, through thoracoscopic methods such as that described herein, visual methods may be used to provide targeted treatment of the intended nerve component(s).

The invention claimed is:

1. A method of treating pulmonary disease, the method comprising:
   (a) inserting an end effector that extends distally from a shaft of an apparatus into a thoracic cavity of a patient by passing at least a portion of the apparatus through a location selected from one of the following: between adjacent ribs, above the sternum, or through the chest wall of the patient, wherein the end effector includes first and second contact components that oppose one other;
   (b) actuating an actuator of a body to simultaneously rotate the first and second contact components that extend distally from the shaft about a hinge point disposed along a longitudinal axis of the shaft to align the first and second contact components of the end effector at least partially around a nerve component present on a bronchial segment, wherein the shaft extends distally from the body; and
   (c) applying energy from a source of energy to at least one of the first and second contact components to the nerve component to treat the nerve component.

2. The method of claim 1, wherein the first and second contact components are first and second substantially semi-circular contact components, wherein aligning the first and second contact components further comprises aligning the first and second substantially semi-circular contact components proximal to or in contact with the nerve component present on the bronchial segment.

3. The method of claim 1, further comprising deforming the first and second contact components to prevent against unintentional squeezing of the bronchial segment.

4. The method of claim 1, wherein the apparatus further comprises a hinge, the method further comprising pivotably articulating the first and second contact components using the hinge.

5. The method of claim 1, wherein actuating the actuator of the body to rotate the first and second contact components further comprises aligning the first and second contact components to be individually moveable with respect to one other to contact an outer surface of the bronchial segment therebetween.

6. The method of claim 1, wherein actuating the actuator of the body to rotate the first and second contact components further comprises aligning the first and second contact components to be in atraumatic engagement with the bronchial segment, wherein applying energy further comprises using the atraumatic engagement to ensure sufficient energy is applied to the nerve component.

7. The method of claim 1, wherein the shaft extends extending proximally from the end effector, wherein rotating at least one of the first and second contact components further comprises rotating the first and second contact components clockwise or counterclockwise around the longitudinal axis defined by the shaft.

8. The method of claim 1, wherein the end effector applies energy in the form of heated elements or electrodes; heated fluid such as gas or liquid; ultrasonic energy, including low-energy ultrasound or high intensity focused ultrasound; harmonic energy; direct current or cauterization exposure; electromagnetic energy; radiofrequency energy; microwaves; plasma energy; infrared; non-ionizing optical energy such as laser treatment including pulsed laser, fractional laser, or high energy laser exposure; or other radiation energy including alpha, beta, gamma, x-ray, proton, neutron, or ionic radiation.

9. The method of claim 1, wherein applying energy further comprises applying mechanical vibration or applying heat using the source of energy and at least one of the first and second contact components to the nerve component to treat the nerve component.

10. The method of claim 1, wherein applying energy further comprises applying energy using pulsed or cyclical electrical signals to electrically treat nerve component with the apparatus.

11. The method of claim 1, wherein the first contact component includes a first bladder containing heated fluid, wherein the second contact component includes a second bladder containing heated fluid, wherein applying energy further comprises heating the nerve component to at least 65 degrees Celsius to treat the nerve component.

12. The method of claim 11, wherein the first contact component includes a first bladder containing heated fluid, wherein the second contact component includes a second bladder containing heated fluid, wherein the method further comprises contacting each of the first and second bladders against the nerve component present on the bronchial segment so that the bronchial segment is disposed between the first and second bladders.

13. The method of claim 1, wherein the first contact component includes a first distal most tip and the second contact component includes a second distal most tip, wherein the first and second distal most tips of the first and second contact components are disposed parallel to one another along the longitudinal axis.

14. The method of claim 1, wherein the first contact component includes a first bladder containing heated fluid, wherein the second contact component includes a second bladder containing heated fluid, wherein the method further comprises contacting each of the first and second bladders against the nerve component present on the bronchial segment so that the bronchial segment is disposed between the first and second bladders.

15. The method of claim 1, wherein the actuator includes a manually actuated trigger, wherein the body includes a handle assembly with a pistol grip, wherein actuating the actuator of the body to simultaneously rotate the first and second contact components further comprises actuating the trigger of the handle assembly to simultaneously rotate the first and second contact components.

16. The method of claim 1, wherein actuating the actuator of the body to rotate the first and second contact components further comprises simultaneously actuating the actuator of the body to rotate the entire end effector around the longitudinal axis defined by the shaft.

17. The method of claim 1, further comprising eluting a neurotoxin from an opening of a fluid bladder disposed on one of the first or second contact components onto the nerve component present on the bronchial segment.

18. A method of treating pulmonary disease, the method comprising:

(a) inserting an end effector that extends from a shaft of an apparatus into a thoracic cavity of a patient by passing at least a portion of the apparatus through a location selected from one of the following: between adjacent ribs, above the sternum, or through the chest wall of the patient, wherein the end effector includes first and second contact components that oppose one other, wherein the first contact component includes a first bladder containing heated fluid, wherein the second contact component includes a second bladder containing heated fluid;

(b) independently rotating one of the first and second bladders of the end effector at least partially around an outer surface of a bronchial segment;

(c) independently rotating the other of the first and second bladders of the end effector at least partially around the outer surface of the bronchial segment such that the first and second contact components at least partially contain the bronchial segment collectively therebetween; and (d) applying energy from a source of energy to at least one of the first and second contact components to a nerve component of the bronchial segment to treat the nerve component.

19. The method of claim 18, further comprising delivering the heated fluid to the first and second bladders through a tube disposed in the shaft.

20. A method of treating pulmonary disease, the method comprising:

(a) inserting an end effector of an apparatus into a thoracic cavity of a patient, wherein the end effector includes first and second contact components that oppose one other, wherein the first contact component includes a first bladder containing heated fluid, wherein the second contact component includes a second bladder containing heated fluid;

(b) aligning the first and second contact components proximal to or in contact with a nerve component present on a bronchial segment by independently rotating one of the first and second bladders of the end effector;

(c) contacting each of the first and second bladders against the nerve component present on the bronchial segment so that the bronchial segment is disposed between the first and second bladders; and (d) applying energy from a source of energy to at least one of the first and second contact components to the nerve component to treat the nerve component.

* * * * *